(12) United States Patent
Ishikawa et al.

(10) Patent No.: US 10,986,818 B2
(45) Date of Patent: Apr. 27, 2021

(54) INFORMATION PROCESSING APPARATUS, INFORMATION PROCESSING METHOD, INFORMATION PROCESSING PROGRAM, DISPLAY CONTROL DEVICE, DISPLAY CONTROL METHOD, AND DISPLAY CONTROL PROGRAM

(71) Applicant: FUJIFILM CORPORATION, Tokyo (JP)

(72) Inventors: Shigetoshi Ishikawa, Kanagawa (JP); Yasuhisa Kaneko, Kanagawa (JP); Haruyasu Nakatsugawa, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/736,839

(22) Filed: Jan. 8, 2020

(65) Prior Publication Data
US 2020/0260694 A1 Aug. 20, 2020

(30) Foreign Application Priority Data
Feb. 18, 2019 (JP) .............................. JP2019-026962

(51) Int. Cl.
*A01K 29/00* (2006.01)
*A61B 5/00* (2006.01)
*A01K 11/00* (2006.01)

(52) U.S. Cl.
CPC .......... *A01K 29/005* (2013.01); *A01K 11/008* (2013.01); *A61B 5/002* (2013.01); *A61B 2503/40* (2013.01)

(58) Field of Classification Search
CPC ............... A01K 29/005; A01K 11/008; A61B 2503/40; G16H 50/00–50/80; G06F 19/30–19/34; G06Q 50/22–50/24
(Continued)

(56) References Cited

U.S. PATENT DOCUMENTS 6,287,254 B1 * 9/2001 Dodds .................... G16B 20/00
600/300
6,910,050 B2 * 6/2005 Pawlick ............... A01K 11/008
379/67.1
(Continued)

FOREIGN PATENT DOCUMENTS

JP 2011-248802 A 12/2011

*Primary Examiner* — Eric Blount
(74) *Attorney, Agent, or Firm* — Solaris Intellectual Property Group, PLLC

(57) ABSTRACT

An information processing apparatus, an information processing method, an information processing program, a display control device, a display control method, and a display control program which are capable of efficiently suppressing a spread of an infection disease are acquired. An information processing apparatus includes an acquisition unit that acquires an inspection result for an animal to be inspected, a determination unit that determines whether or not an owner of the animal to be inspected raises a plurality of animals, and a notification unit that notifies the owner of information indicating that the animal to be inspected is infected with an infection disease in a case where the inspection result indicates that the animal to be inspected is infected with the infection disease and it is determined that the owner raises the plurality of animals.

10 Claims, 9 Drawing Sheets

(58) Field of Classification Search
USPC .......................................... 340/573.1–573.6
See application file for complete search history.

(56) References Cited

U.S. PATENT DOCUMENTS

| | | | | |
|---|---|---|---|---|
| 7,548,839 B2* | 6/2009 | Dodds | ................... | G16B 50/00 703/3 |
| 7,810,451 B2* | 10/2010 | Pratt | ................... | G06Q 10/0833 119/174 |
| 8,736,440 B2* | 5/2014 | Kwak | ................... | A01K 11/006 340/539.12 |
| 8,866,605 B2* | 10/2014 | Gibson | ................ | A01K 11/006 340/539.1 |
| 9,202,193 B2* | 12/2015 | Kwak | ................ | G06Q 10/0833 |
| 9,298,756 B1* | 3/2016 | Johnson | .............. | G06F 16/9554 |
| 10,058,076 B2* | 8/2018 | Han | ....................... | H04N 7/183 |
| 10,188,048 B2* | 1/2019 | Nelson | ................ | H04W 4/029 |
| 10,691,674 B2* | 6/2020 | Leong | ................ | G06F 21/6209 |
| 2006/0201432 A1* | 9/2006 | Pratt | ..................... | G06Q 50/02 119/51.02 |
| 2007/0288249 A1* | 12/2007 | Rowe | ..................... | A01K 29/00 705/7.11 |
| 2012/0124387 A1* | 5/2012 | Skocic | ................... | G16H 10/60 713/186 |
| 2012/0326874 A1* | 12/2012 | Kwak | .................. | A01K 11/006 340/573.3 |
| 2013/0285815 A1* | 10/2013 | Jones, II | .............. | A01K 11/006 340/573.3 |
| 2014/0046698 A1* | 2/2014 | Skocic | ................. | A01K 11/006 705/3 |
| 2016/0246934 A1* | 8/2016 | Dunlop | ................... | H04L 67/32 |
| 2017/0091403 A1* | 3/2017 | Maher | ................... | G06F 19/3456 |
| 2018/0218057 A1* | 8/2018 | Beckham | ............... | G06Q 50/02 |
| 2019/0053470 A1* | 2/2019 | Singh | ................... | A01K 11/006 |
| 2019/0082654 A1* | 3/2019 | Robbins | ............... | A01K 29/005 |
| 2019/0183096 A1* | 6/2019 | Moreno | ................ | A23K 50/00 |
| 2020/0242655 A1* | 7/2020 | Brown | ................ | G06Q 30/018 |

* cited by examiner

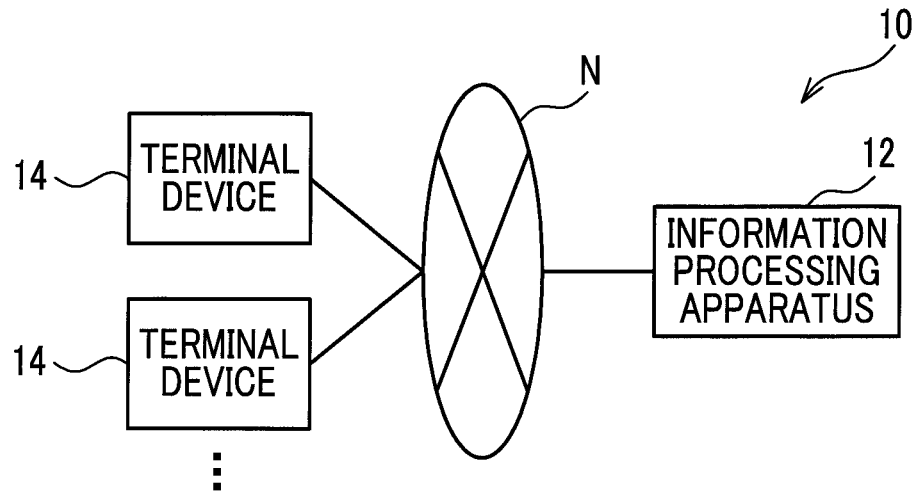
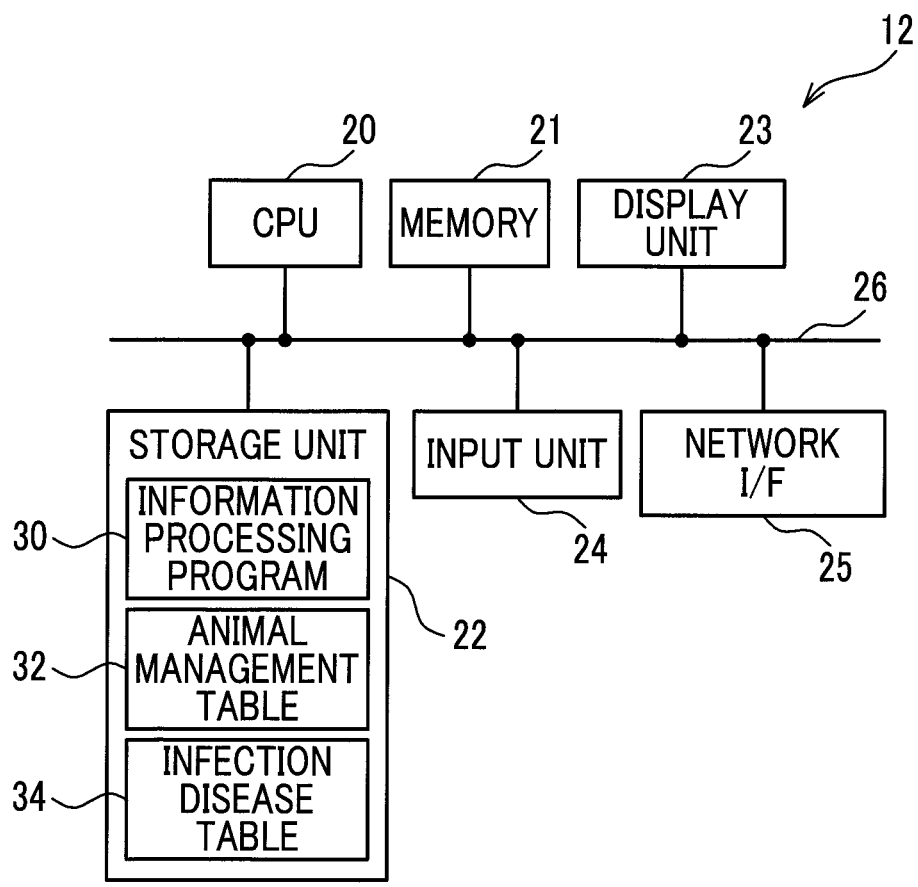

FIG. 3

| OWNER INFORMATION | | | ... | ANIMAL INFORMATION | | | | | | |
|---|---|---|---|---|---|---|---|---|---|---|
| ID | NAME | CONTACT INFORMATION | | ID | NAME | GENDER | AGE | RACE | BREED | ... |
| A100 | AAA | aaa@bbb | ... | B100 | TARO | MALE | 7 | DOG | CHIHUAHUA | ... |
| | | | | B101 | JIRO | MALE | 4 | DOG | POODLE | ... |
| | | | | ... | ... | ... | ... | ... | ... | ... |
| A101 | BBB | ccc@ddd | ... | B105 | HANA | FEMALE | 3 | CAT | PERSIAN | ... |
| ... | ... | ... | ... | ... | ... | ... | ... | ... | ... | ... |

32

| DISEASE NAME | RACE | 34 |
|---|---|---|
| INFECTION DISEASE A | DOG | |
| INFECTION DISEASE B | CAT | |
| INFECTION DISEASE C | DOG, CAT, HUMAN | |
| ... | ... | |

| ID | NAME | GENDER | AGE | RACE | BREED | IMAGE | ... |
|---|---|---|---|---|---|---|---|
| B100 | TARO | MALE | 7 | DOG | CHIHUAHUA | /img/a.jpg | ... |
| B101 | JIRO | MALE | 4 | DOG | POODLE | /img/b.jpg | ... |
| ... | ... | ... | ... | ... | ... | ... | ... |

INFORMATION PROCESSING APPARATUS, INFORMATION PROCESSING METHOD, INFORMATION PROCESSING PROGRAM, DISPLAY CONTROL DEVICE, DISPLAY CONTROL METHOD, AND DISPLAY CONTROL PROGRAM

CROSS-REFERENCE TO RELATED APPLICATION

This application claims priority under 35 USC 119 from Japanese Patent Application No. 2019-026962 filed Feb. 18, 2019, the disclosure of which is incorporated by reference herein.

BACKGROUND

Technical Field

The present disclosure relates to an information processing apparatus, an information processing method, an information processing program, a display control device, a display control method, and a display control program.

Related Art

An infection monitoring system that notifies participants in the system that the participants are suspected of being infected with a virus is disclosed (see JP2011-248802A). The infection monitoring system acquires an infection estimation date and time which is a date and time when it is estimated that a person infected with a virus is infected with the virus from a hospital. The infection monitoring system performs the aforementioned notification for the participants closes to the infected person within a predetermined distance after the infection estimation date and time.

SUMMARY

Incidentally, there is an owner who raises a plurality of animals. For example, in a case where some animals of the plurality of animals raised by the owner are infected with an infection disease, the infection disease is relatively highly likely to infect other animals living within a relatively narrow range such as the same house. In this case, in a case where the owner can be notified that some animals are infected with the infection disease, a spread of the inspection disease is preferably suppressed.

However, in a technology described in JP2011-248802A, it is necessary to perform a troublesome process using positional information of an infected person and a participant of system other than the infected person in order to notify the participant of the system that the participant is suspected to be inspected with a virus. Accordingly, it is not possible to efficiently suppress the spread of the infection disease.

The present display control has been made in view of the aforementioned circumstances, and an object of the present disclosure is to provide an information processing apparatus, an information processing method, an information processing program, a display control device, a display control method, and a display control program which are capable of efficiently suppressing a spread of an infection disease.

In order to achieve the object, an information processing apparatus of the present disclosure comprises an acquisition unit that acquires an inspection result for an animal to be inspected, a determination unit that determines whether or not an owner of the animal to be inspected raises a plurality of animals, and a notification unit that notifies the owner of information indicating that the animal to be inspected is infected with an infection disease in a case where the inspection result indicates that the animal to be inspected is infected with the infection disease and it is determined that the owner raises the plurality of animals.

In the information processing apparatus of the present disclosure, the determination unit may further determine whether or not the infection disease is likely to infect an animal other than the animal to be inspected among the plurality of animals raised by the owner, and the notification unit may further notify of information indicating whether or not the infection disease is likely to infect the animal other than the animal to be inspected among the plurality of animals raised by the owner.

In the information processing apparatus of the present disclosure, the determination unit may further determine whether or not the infection disease is likely to infect human, and the notification unit may further notify of information indicating whether or not the infection disease is likely to infect human.

A display control device of the present disclosure comprises a reception unit that receives information which is notified from an information processing apparatus and indicates that an animal is infected with an infection disease, and a display controller that performs control for displaying images of a plurality of animals in a state in which it is possible to discriminate which animal of the plurality of animals is infected with the infection disease based on the information received by the reception unit.

An information processing method of the present disclosure is executed by a computer. The method comprises acquiring an inspection result for an animal to be inspected, determining whether or not an owner of the animal to be inspected raises a plurality of animals, and notifying the owner of information indicating that the animal to be inspected is infected with an infection disease in a case where the inspection result indicates that the animal to be inspected is infected with the infection disease and it is determined that the owner raises the plurality of animals.

An information processing program of the present disclosure causes a computer to execute processes of acquiring an inspection result for an animal to be inspected, determining whether or not an owner of the animal to be inspected raises a plurality of animals, and notifying the owner of information indicating that the animal to be inspected is infected with an infection disease in a case where the inspection result indicates that the animal to be inspected is infected with the infection disease and it is determined that the owner raises the plurality of animals.

A display control method of the present disclosure is executed by a computer. The method comprises receiving information which is notified from an information processing apparatus and indicates that an animal is infected with an infection disease, and performing control for displaying images of a plurality of animals so as to discriminate which animal of the plurality of animals is infected with the infection disease based on the received information.

A display control program of the present disclosure causes a computer to execute processes of receiving information which is notified from an information processing apparatus and indicates that an animal is infected with an infection disease, and performing control for displaying images of a plurality of animals so as to discriminate which animal of the plurality of animals is infected with the infection disease based on the received information.

An information processing apparatus of the present disclosure comprises a memory that stores a command to be executed on a computer, and a processor that is configured to execute the stored command. The processor acquires an inspection result for an animal to be inspected, determines whether or not an owner of the animal to be inspected raises a plurality of animals, and notifies the owner of information indicating that the animal to be inspected is infected with an infection disease in a case where the inspection result indicates that the animal to be inspected is infected with the infection disease and it is determined that the owner raises the plurality of animals.

A display control device of the present disclosure comprises a memory that stores a command to be executed on a computer, and a processor that is configured to execute the stored command. The processor receives information which is notified from an information processing apparatus and indicates that an animal is infected with an infection disease, and performs control for displaying images of a plurality of animals in a state in which it is possible to discriminate which animal of the plurality of animals is infected with the infection disease based on the information received by the reception unit.

According to the present disclosure, it is possible to efficiently suppress a spread of an infection disease.

BRIEF DESCRIPTION OF THE DRAWINGS

Exemplary Embodiments of the present disclosure will be described in detail with reference to the following figures, wherein:

FIG. 1 is a block diagram showing an example of a configuration of an information processing system according to an embodiment.

FIG. 2 is a block diagram showing an example of a hardware configuration of an information processing apparatus according to the embodiment.

FIG. 3 is a diagram showing an example of an animal management table according to the embodiment.

DETAILED DESCRIPTION

Figures 4, 5:
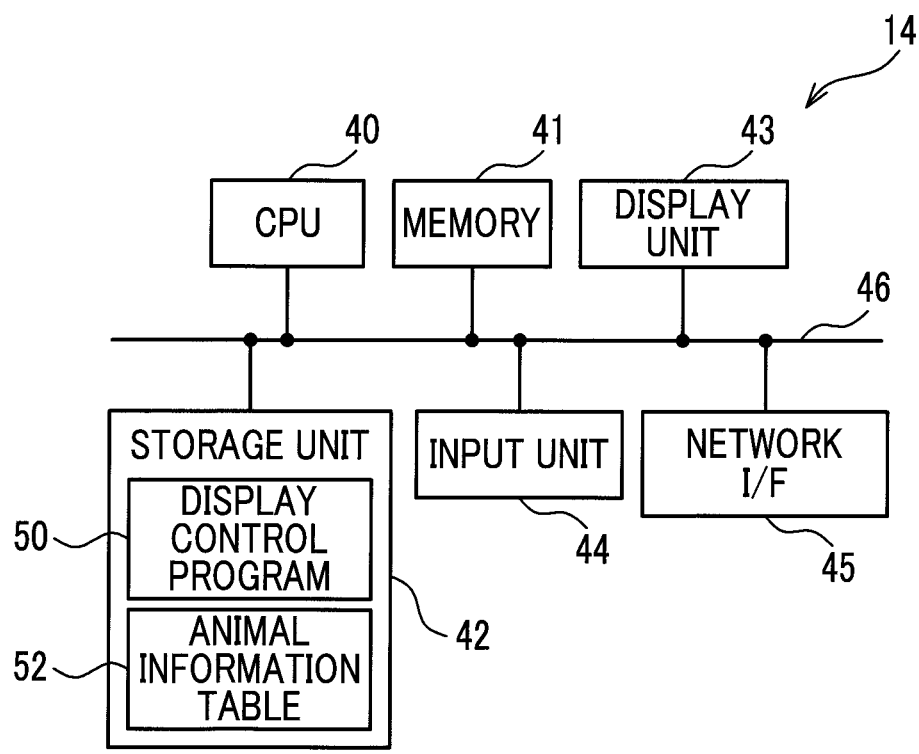
FIG. 4 is a diagram showing an example of an infection disease table according to the embodiment.
FIG. 5 is a block diagram showing an example of a hardware configuration of a terminal device according to the embodiment.

Hereinafter, form examples for implementing a technology of the present disclosure will be described in detail.

Initially, a configuration of an information processing system 10 according to the present embodiment will be described with reference to FIG. 1. As shown in FIG. 1, the information processing system 10 includes an information processing apparatus 12 and a plurality of terminal devices 14. The information processing apparatus 12 and the plurality of terminal devices 14 are connected to a network N, and can communicate with each other via the network N.

For example, the information processing apparatus 12 is provided in an animal hospital. Examples of the information processing apparatus 12 include a server computer. The information processing apparatus 12 may be a cloud server. For example, the terminal device 14 is owned by an owner of an animal such as a pet. Examples of the terminal device 14 include a smartphone and a tablet computer. The terminal device 14 is an example of a display control device according to a disclosed technology. The "animal" in the present specification means an animal such as a dog and a cat except for "human".

Next, a hardware configuration of the information processing apparatus 12 according to the present embodiment will be described with reference to FIG. 2. As shown in FIG. 2, the information processing apparatus 12 includes a central processing unit (CPU) 20, a memory 21 as a temporary storage region, and a nonvolatile storage unit 22. The information processing apparatus 12 includes a display unit 23 such as a liquid crystal display, an input unit 24 such as a keyboard and a mouse, and a network interface (I/F) 25 connected to the network N. The CPU 20, the memory 21, the storage unit 22, the display unit 23, the input unit 24, and the network I/F 25 are connected to a bus 26.

The storage unit 22 is implemented by a hard disk drive (HDD), a solid state drive (SSD), and a flash memory. An information processing program 30 is stored in the storage unit 22 as a storage medium. The CPU 20 reads out the information processing program 30 from the storage unit 22, develops the readout information processing program into the memory 21, and executes the developed information processing program 30. An animal management table 32 and an infection disease table 34 are stored in the storage unit 22.

FIG. 3 shows an example of the animal management table 32. The animal management table 32 is a table for managing owners of animals and animals raised by the owners. As shown in FIG. 3, information (hereinafter, referred to as "owner information") regarding the owner of the animal and information (hereinafter, referred to as "animal information") regarding the animal are stored in association with each other in the animal management table 32.

The owner information includes an identifier (ID) as an example of identification information of the owner, a name, and contact information. Although it has been described in the present embodiment that an electronic mail address is applied as the contact information, the present invention is not limited thereto. As the contact information, a messaging service ID may be applied, an account ID of a social networking service (SNS) may be applied, or a telephone number may be applied.

The animal information includes an ID as an example of identification information of the animal raised by the owner indicated by the corresponding owner information, a name, a gender, an age, a race, and a breed. In a case where one owner raises a plurality of animals, a plurality of animal information items is associated with one owner information.

FIG. 4 shows an example of the infection disease table 34. The infection disease table 34 is a table for managing a target that is likely to be infected with an infection disease. As shown in FIG. 4, in the infection disease table 34, a race of the animal that is likely to be infected with the infection disease is stored for each infection disease. In addition to the animal, "human" in addition to the race of the animal is stored in a race column for an infection disease that is likely to infect human.

Examples of an infection disease that infects only cats include feline panleukopenia, feline leukemia virus infection, feline immunodeficiency virus infection, feline infectious peritonitis, and feline cold. Examples of an infection disease that infects only dogs include canine kennel cough, canine distemper virus infection, canine parvovirus infection, and canine adenovirus infection. Examples of an infection disease that infects both dogs and cats and infects humans include dog and cat roundworm larva migration and dermatophytosis.

Next, a hardware configuration of the terminal device 14 according to the present embodiment will be described with reference to FIG. 5. As shown in FIG. 5, the terminal device 14 includes a CPU 40, a memory 41 as a temporary storage region, and a nonvolatile storage unit 42. The terminal device 14 includes a display unit 43 such as a liquid crystal display, an input unit 44 such as a touch panel, and a network I/F 45 that manages connection to the network N through wireless communication. The CPU 40, the memory 41, the storage unit 42, the display unit 43, the input unit 44, and the network I/F 45 are connected to a bus 46.

The storage unit 42 is realized by a flash memory. A display control program 50 is stored in the storage unit 42 as a storage medium. The CPU 40 reads out the display control program 50 from the storage unit 42, develops the readout control program into the memory 41, and executes the developed display control program 50. An animal information table 52 is stored in the storage unit 42.

Figures 6, 7:
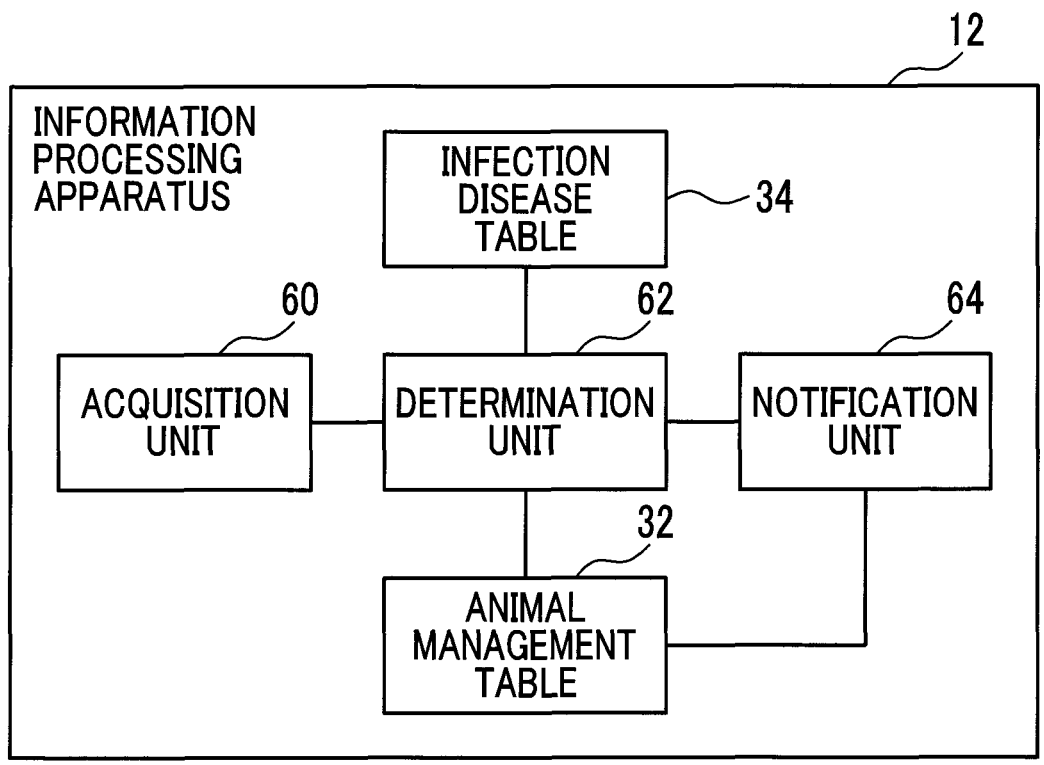
FIG. 6 is a diagram showing an example of an animal information table according to the embodiment.
FIG. 7 is a block diagram showing an example of a functional configuration of the information processing apparatus according to the embodiment.

FIG. 6 shows an example of the animal information table 52. The animal information table 52 is table in which information regarding the animal raised by the owner who owns the terminal device 14 is stored. As shown in FIG. 6, the same information as the animal information of the animal management table 32 is stored for the animal raised by the owner in the animal information table 52. A storage path of image data indicating an image of the animal is also stored in the animal information table 52.

Next, a functional configuration of the information processing apparatus 12 according to the present embodiment will be described with reference to FIG. 7. As shown in FIG. 7, the information processing apparatus 12 includes an acquisition unit 60, a determination unit 62, and a notification unit 64. The CPU 20 executes the information processing program 30, and thus, the information processing program functions as the acquisition unit 60, the determination unit 62, and the notification unit 64.

In a case where the animal to be inspected is suspected of being infected with the infection disease, a veterinarian of the animal hospital according to the present embodiment requests a diagnosis by collecting a specimen from the animal and transmitting the collected specimen to an external inspection agency, for example. In a case where the inspection in the inspection agency is completed, information indicating an inspection result is transmitted to the information processing apparatus 12 from the inspection agency, and the information processing apparatus 12 receives the information indicating the inspection result transmitted from the external inspection agency. The information indicating the inspection result includes the ID of the animal to be inspected, and includes a disease name of the infection disease in a case where the animal is infected with the infection disease. The information indicating the inspection result may be input by the veterinarian of the animal hospital through the input unit 24.

The acquisition unit 60 acquires information indicating the inspection result for the animal to be inspected which is transmitted from the inspection agency. The determination unit 62 determines whether or not the owner of the animal to be inspected raises a plurality of animals while referring to the animal management table 32.

In a case where the inspection result indicated by the information acquired by the acquisition unit 60 indicates that the animal is infected with the infection disease and the owner of the animal to be inspected raises the plurality of animals, the determination unit 62 extracts the disease name of the infection disease from the information indicating the inspection result. The determination unit 62 determines whether or not the infection disease of the extracted disease name is likely to infect an animal other than the animal to be inspected among the plurality of animals raised by the owner while referring the animal management table 32 and the infection disease table 34. Hereinafter, the animal to be inspected is referred to as a "first animal", and the animal other than the first animal of the plurality of animals raised by the owner is referred to as a "second animal". Specifically, the determination unit 62 determines whether or not the race of the second animal is a race of an animal that is likely to be infected with the infection disease that infects the first animal.

The determination unit 62 determines whether or not the infection disease that infects the first animal is likely to infect human while referring to the infection disease table 34.

In a case where the inspection result for the first animal indicates that the first animal is infected with the infection disease and it is determined that the owner of the first animal raises the plurality of animals, the notification unit 64 acquires the contact information of the owner of the first animal while referring to the animal management table 32. The notification unit 64 notifies the owner of information indicating that the first animal is infected with the infection disease by transmitting information including the animal ID of the first animal and the disease name of the infection disease of the first animal to the acquired contact information.

The notification unit 64 notifies the owner by transmitting information indicating whether or not the infection disease of the first animal is likely to infect the second animal as the determination result of the determination unit 62 to the acquired contact information. The notification unit 64 notifies the owner by transmitting information indicating whether or not the infection disease of the first animal is likely to infect human as the determination result of the determination unit 62 to the acquired contact information.

Although it has been described in the present embodiment that the test data is applied as the information to be notified by the notification unit 64, the present invention is not limited thereto. As the information to be notified by the notification unit 64, sound data may be applied, or both the text data and the sound data may be applied.

Figure 8:
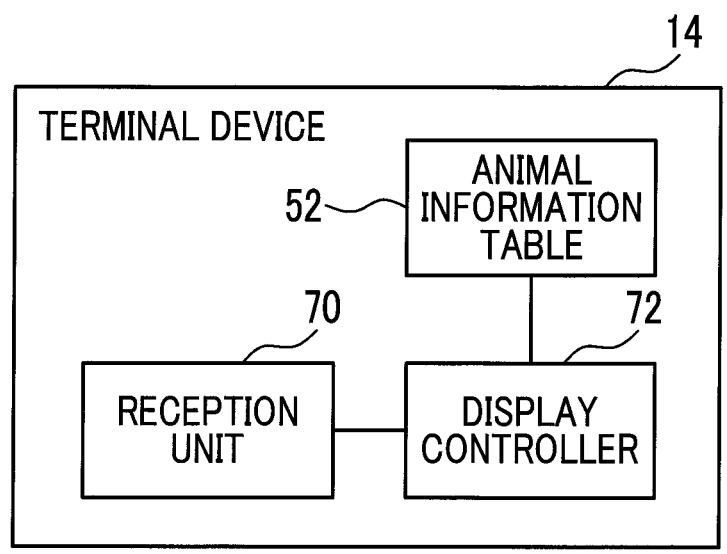
FIG. 8 is a block diagram showing an example of a functional configuration of the terminal device according to the embodiment.

Next, a functional configuration of the terminal device 14 according to the present embodiment will be described with reference to FIG. 8. As shown in FIG. 8, the terminal device 14 includes a reception unit 70 and a display controller 72. The CPU 40 executes the display control program 50, and the display control program functions as the reception unit 70 and the display controller 72.

The reception unit 70 receives the information which is notified from the information processing apparatus 12 and indicates that the first animal is infected with the infection disease. The reception unit 70 receives the information which is notified from the information processing apparatus 12 and indicates whether or not the infection disease is likely to infect the second animal. The reception unit 70 receives the information which is notified from the information processing apparatus 12 and indicates whether or not the infection disease is likely to infect human.

The display controller 72 performs control for displaying images of the plurality of animals in a state in which it is possible to discriminate which animal of the plurality of animals is infected with the infection disease based on the information received by the reception unit 70.

In the present embodiment, the display controller 72 performs control for displaying images of all the animals on the display unit 43 in a state in which it is possible to discriminate which animal of all the animals stored in the animal information table 52 is infected with the infection disease while referring to the animal information table 52. The display controller 72 performs control for displaying the information indicating whether or not the infection disease of the first animal is likely to infect the second animal on the display unit 43. The display controller 72 performs control for displaying the information indicating whether or not the infection disease is likely to infect human on the display unit 43.

Figure 9:
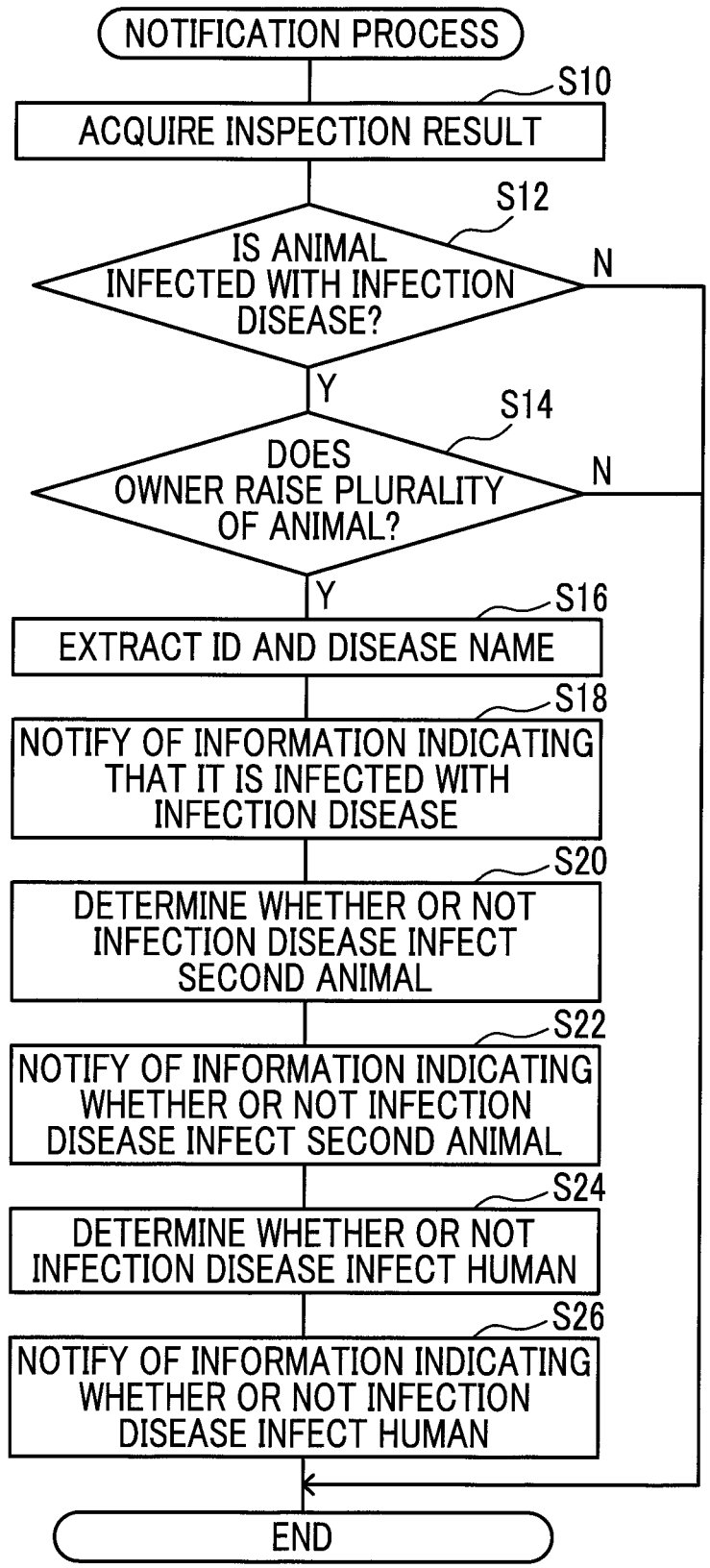
FIG. 9 is a flowchart showing an example of a notification process according to the embodiment.

Next, the actions of the information processing apparatus 12 according to the present embodiment will be described with reference to FIG. 9. The CPU 20 executes the information processing program 30, and thus, a notification process shown in FIG. 9 is performed. For example, the notification process shown in FIG. 9 is performed in a case where the information indicating the inspection result transmitted from the inspection agency is received by the information processing apparatus 12.

In step S10 of FIG. 9, the acquisition unit 60 acquires the information indicating the inspection result for the first animal transmitted from the inspection agency. In step S12, the determination unit 62 determines whether or not the inspection result indicated by the information acquired through the process of step S10 indicates that the first animal is infected with the infection disease. In a case where this determination is a positive determination, the process proceeds to step S14. In step S14, the determination unit 62 determines whether or not the owner of the first animal raises the plurality of animals while referring to the animal management table 32. In a case where this determination is a positive determination, the process proceeds to step S16.

In step S16, the determination unit 62 extracts the ID of the first animal and the disease name of the infection disease from the information acquired through the process of step S10. In step S18, the notification unit 64 acquires the contact information of the owner of the first animal while referring to the animal management table 32. As stated above, the notification unit 64 notifies the acquired contact information of the information indicating that the first animal is infected with the infection disease.

In step S20, the determination unit 62 determines whether or not the infection disease of the disease name extracted through the process of step S16 is likely to infect the second animal of the plurality of animals raised by the owner while referring to the animal management table 32 and the infection disease table 34. In step S22, the notification unit 64 notifies the owner by transmitting the information indicating whether or not the infection disease of the first animal is likely to infect the second animal as the determination result of the process of step S20 to the contact information acquired through the process of step S18.

In step S24, the determination unit 62 determines whether or not the infection disease of the first animal is likely to infect human while referring to the infection disease table 34. In step S26, the notification unit 64 notifies the owner by transmitting the information indicating whether or not the infection disease of the first animal is likely to infect human as the determination result of the process of step S24 to the contact information acquired through the process of step S18. In a case where the process of step S26 is ended, the present notification process is ended. Meanwhile, the present notification process is ended even in a case where the determination of step S12 is a negative determination. The present notification process is ended even in a case where the determination of step S14 is a negative determination.

Figure 10:
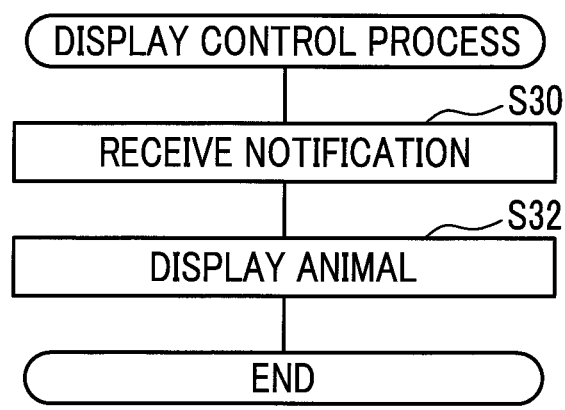
FIG. 10 is a flowchart showing an example of a display control process according to the embodiment.

Next, the actions of the terminal device 14 according to the present embodiment will be described with reference to FIG. 10. The CPU 40 executes the display control program 50, and thus, a display control process shown in FIG. 10 is performed. For example, the display control process shown in FIG. 10 is performed in a case where the information which is notified from the information processing apparatus 12 and indicates that the first animal is infected with the infection disease is received by the terminal device 14.

In step S30 of FIG. 10, the information which is notified from the information processing apparatus 12 through the process of step S18 and indicates that the first animal is infected with the infection disease is received. The reception unit 70 receives the information which is notified from the information processing apparatus 12 through the process of step S22 and indicates that the infection disease is likely to infect the second animal. The reception unit 70 receives the information which is notified from the information processing apparatus 12 through the process of step S26 and indicates whether or not the infection disease is likely to infect human.

In step S32, the display controller 72 performs control for displaying the images of all the animals on the display unit 43 in a state in which it is possible to discriminate which animal of all the animals stored in the animal information table 52 is infected with the infection disease while referring to the animal information table 52. The display controller 72 performs control for displaying the information indicating whether or not the infection disease of the first animal is likely to infect the second animal on the display unit 43. The display controller 72 performs control for displaying the information indicating whether or not the infection disease is likely to infect human on the display unit 43. In a case where the process of step S32 is ended, the present display control process is ended.

Figure 11:
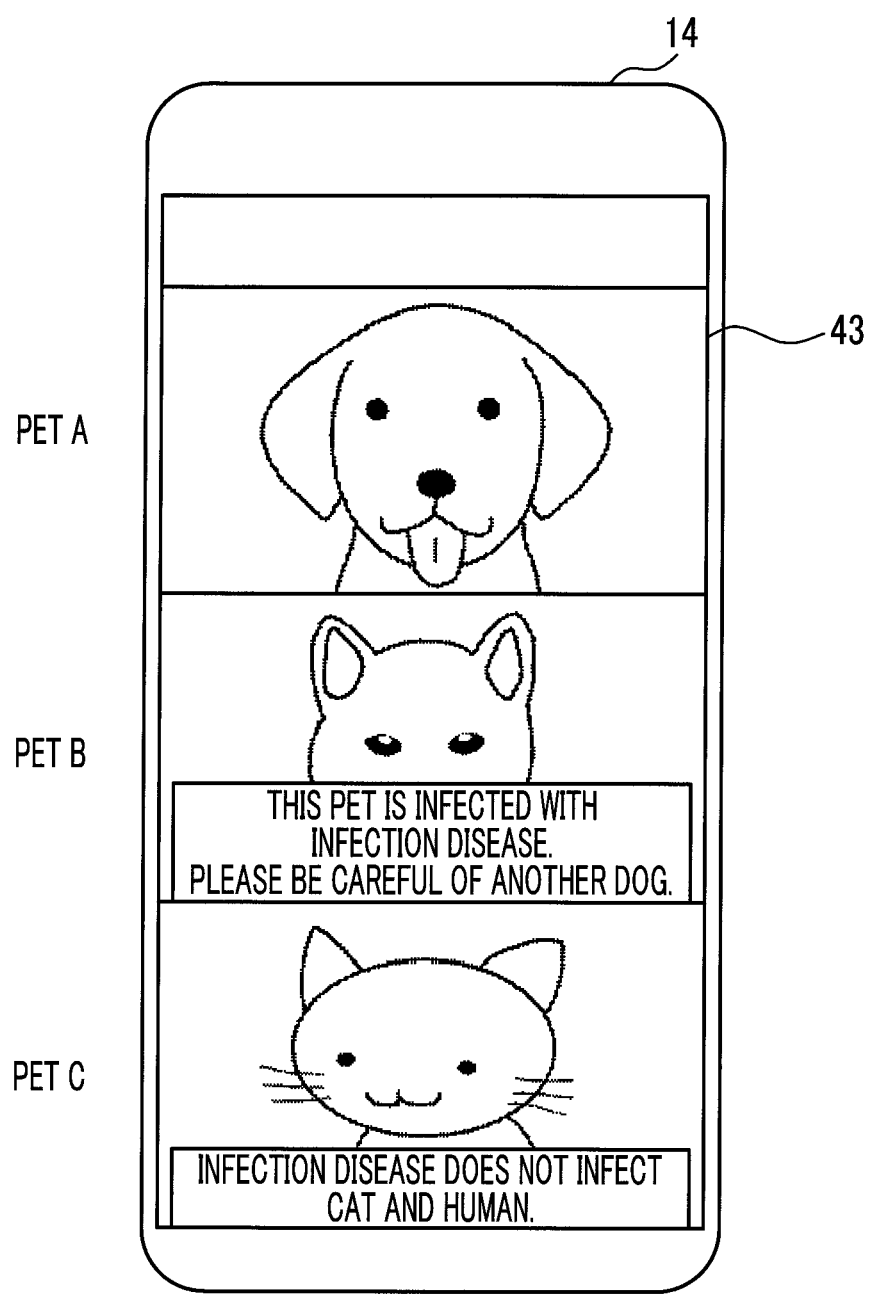
FIG. 11 is a diagram showing an example of a display screen according to the embodiment.

For example, as shown in FIG. 11, the images of all the animals raised by the owner are vertically displayed on the display unit 43 through the process of step S32. In FIG. 11, an example in which the owner raises three pets A, B, and C, the race of the pets A and B is a dog, and the race of the pet C is a cat is illustrated. In FIG. 11, an example in which the pet B is the first animal infected with the infection disease and the pets A and C are the second animals other than the first animal of all the animals raised by the owner is illustrated. In FIG. 11, an example in which the infection disease of the pet B infects only the dog and does not infect the cat and human is illustrated.

As shown in FIG. 11, in the present embodiment, a message indicating that the pet is infected with the infection disease is displayed so as to be superimposed on an image of the pet B, and thus, it is possible to discriminate that the pet B is infected with the infection disease. In the example of FIG. 11, a message for warning that the infection disease is likely to infect another dog is displayed. A message indicating that the infection disease does not infect the cat and human is displayed in the example of FIG. 11.

Figure 12:
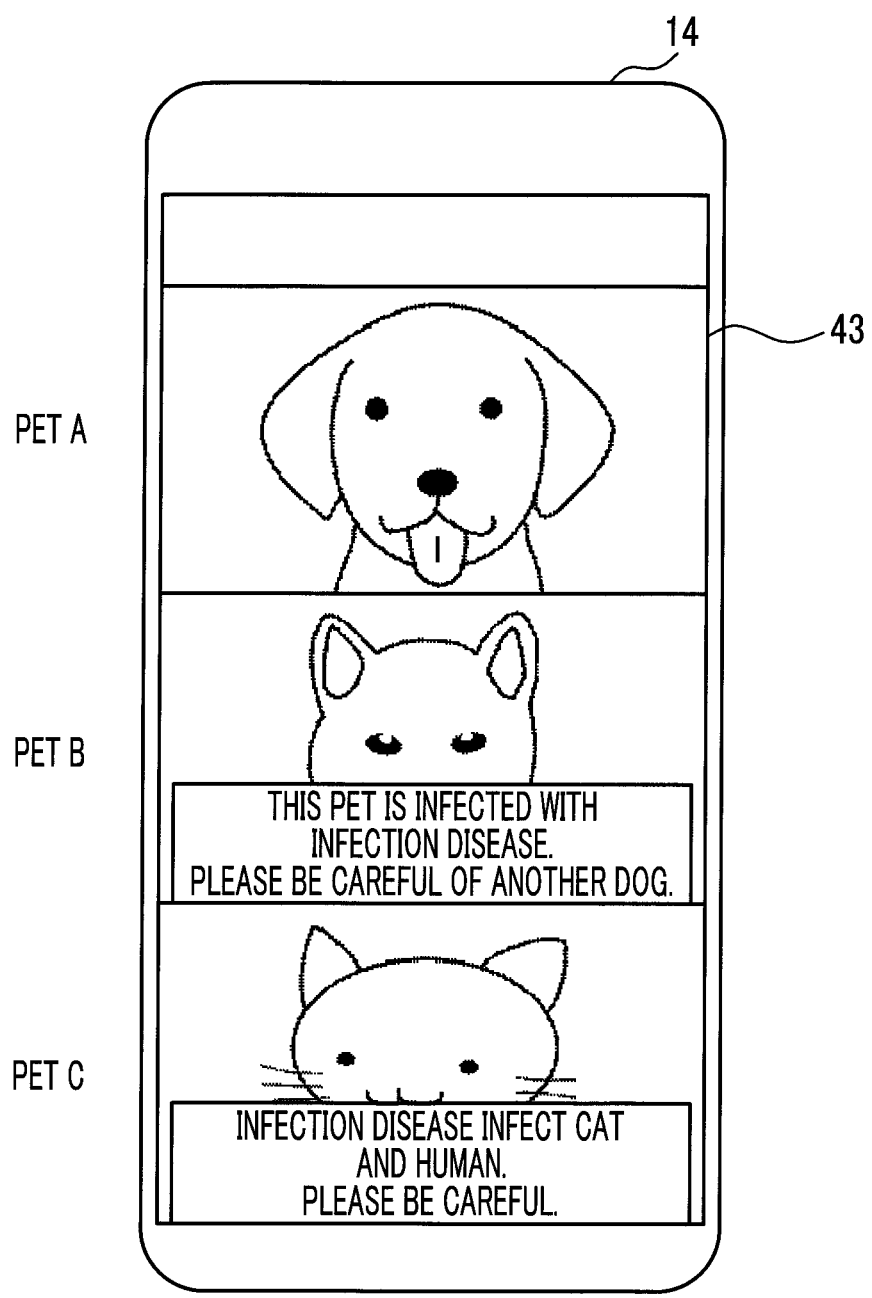
FIG. 12 is a diagram showing an example of a display screen according to the embodiment.

An example of a display screen in a case where the infection disease infects a cat and human in the example of FIG. 11 is shown in FIG. 12. In this case, as shown in FIG. 12, a message indicating that the infection disease infects the cat and human and a message for warning are displayed instead of the message indicating that the infection disease does not infect the cat and human in FIG. 11.

As described above, according to the present embodiment, in a case where the inspection result indicates that the animal to be inspected is infected with the infection disease and it is determined that the owner raises the plurality of animals, the information indicating that the animal to be inspected is infected with the infection disease is notified to the owner. Accordingly, it is possible to perform the aforementioned notification without performing a troublesome process using positional information, and thus, it is possible to efficiently suppress a spread of the infection disease.

According to the present embodiment, the information indicating whether or not the infection disease of the first animal is likely to infect the second animal is notified. Accordingly, the owner can ascertain whether or not the infection disease is likely to infect the second animal.

According to the present embodiment, the information indicating whether or not the infection disease of the first animal is likely to infect human is notified. Accordingly, the owner can ascertain whether or not the owner himself or herself is likely to be infected with the infection disease.

In the aforementioned embodiment, information regarding a family of the owner may be further stored in the owner information of the animal management table 32. In this case, the notification unit 64 may also transmit the notification for the owner performed in step S18, S22, or S26 of the notification process shown in FIG. 9 to the family of the owner. In this case, a display screen shown in FIG. 11 or 12 is displayed on the display unit 43 of the terminal device 14 owned by the family of the owner. In this form example, even in a case where the owner is away from home, the family at home can take countermeasures to suppress the spread of the infection disease to other animals. In a case where the countermeasures to suppress the spread of the infection disease in this case are completed, the terminal device 14 owned by the person who takes the countermeasures may transmit a message indicating that the countermeasures are completed to the terminal device 14 owned by the family.

In the aforementioned embodiment, for example, in a case where the owner performs an operation for designating the first animal infected with the infection disease on the display screen shown in FIG. 11 or 12, the screen transits to a diagnosis reservation screen for reserving a diagnosis date and time of the animal hospital.

In the embodiment, for example, various processors to be described below can be used as hardware structures of the processing units that perform various processes such as the acquisition unit 60, the determination unit 62, the notification unit 64, the reception unit 70, and the display controller 72. As stated above, examples of various processors include a programmable logic device (PLD) such as a FPGA which is a processor of which a circuit configuration can be changed after being manufactured, a dedicated electric circuit such as an application specific integrated circuit (ASIC) which is a processor having a circuit configuration designed as a dedicated circuit in order to perform a specific process in addition to the CPU which is a general-purpose processor functioning as various processing units by executing software (program).

One processing unit may be constituted by one of these various processors, or may be constituted by a combination (for example, a combination of a plurality of FPGAs or a combination of the CPU and the FPGA) of the same kind or different kinds of two or more processors. Alternatively, the plurality of processing units may be constituted by one processor. Firstly, as the example in which the plurality of processing units is constituted by one processor, there is a form in which one processor is constituted by a combination of one or more CPUs and software and this processor functions as the plurality of processing units as represented by computers such as a client and a server. Secondly, there is a form in which a processor that implements the entire system function including the plurality of processing units by one integrated circuit (IC) chip as represented by a system on chip (SoC) is used. As stated above, various processing units are constituted as hardware structure by using one or more of various processors.

More specifically, an electric circuitry acquired by combining circuit elements such as semiconductor elements can be used as the hardware structure of these various processors.

Although the aspect in which the information processing program 30 is stored (installed) in advance in the storage unit 22 has been described in the embodiment, the present disclosure is not limited thereto. The information processing program 30 may be provided while being recorded in a recording medium such as a compact disc read only memory (CD-ROM), a digital versatile disc read only memory (DVD-ROM), and a universal serial bus (USB) memory. The information processing program 30 may be downloaded from an external device via a network.

Although the aspect in which the display control program 50 is stored (installed) in advance in the storage unit 42 has been described in the embodiment, the present disclosure is not limited thereto. The display control program 50 may be provided while being recorded in a recording medium such as CD-ROM, DVD-ROM, and USB memory. The display control program 50 may be downloaded from an external device via a network.

What is claimed is:

1. An information processing apparatus comprising:
an acquisition unit that acquires an inspection result for an animal to be inspected;
a determination unit that determines whether or not an owner of the animal to be inspected raises a plurality of animals; and
a notification unit that notifies the owner of information indicating that the animal to be inspected is infected with an infection disease in a case where the inspection result indicates that the animal to be inspected is infected with the infection disease and it is determined that the owner raises the plurality of animals,
wherein the determination unit further determines whether or not the infection disease is likely to infect an animal other than the animal to be inspected among the plurality of animals raised by the owner, and
the notification unit further notifies the owner of information indicating whether or not the infection disease is likely to infect the animal other than the animal to be inspected among the plurality of animals raised by the owner, wherein the animal other than the animal to be inspected is a different breed or species from the animal to be inspected.

2. The information processing apparatus according to claim 1,
wherein the determination unit further determines whether or not the infection disease is likely to infect a human, and
the notification unit further notifies of information indicating whether or not the infection disease is likely to infect a human.

3. A display control device comprising:
a reception unit that receives information which is notified from an information processing apparatus and indicates that an animal is infected with an infection disease; and
a display controller that performs control for displaying images of a plurality of animals that an owner raises in a state in which it is possible to discriminate which animal of the plurality of animals that the owner raises is infected with the infection disease based on the information received by the reception unit, in a case where it is determined that the owner raises the plurality of animals, wherein the plurality of animals that the owner raises include a plurality of different breeds, species or a combination thereof.

4. An information processing method executed by a computer, the method comprising:
acquiring an inspection result for an animal to be inspected;
determining whether or not an owner of the animal to be inspected raises a plurality of animals;
notifying the owner of information indicating that the animal to be inspected is infected with an infection disease in a case where the inspection result indicates that the animal to be inspected is infected with the infection disease and it is determined that the owner raises the plurality of animals;
determining whether or not the infection disease is likely to infect an animal other than the animal to be inspected among the plurality of animals raised by the owner; and
notifying the owner of information indicating whether or not the infection disease is likely to infect the animal other than the animal to be inspected among the plurality of animals raised by the owner, wherein the animal other than the animal to be inspected is a different breed or species from the animal to be inspected.

5. A non-transitory recording medium recording an information processing program causing a computer to execute processes of:
acquiring an inspection result for an animal to be inspected;
determining whether or not an owner of the animal to be inspected raises a plurality of animals;
notifying the owner of information indicating that the animal to be inspected is infected with an infection disease in a case where the inspection result indicates that the animal to be inspected is infected with the infection disease and it is determined that the owner raises the plurality of animals;
determining whether or not the infection disease is likely to infect an animal other than the animal to be inspected among the plurality of animals raised by the owner; and
notifying the owner of information indicating whether or not the infection disease is likely to infect the animal other than the animal to be inspected among the plurality of animals raised by the owner, wherein the animal other than the animal to be inspected is a different breed or species from the animal to be inspected.

6. A display control method executed by a computer, the method comprising:
receiving information which is notified from an information processing apparatus and indicates that an animal is infected with an infection disease; and
performing control for displaying images of a plurality of animals that an owner raises so as to discriminate which animal of the plurality of animals that the owner raises is infected with the infection disease based on the received information, in a case where it is determined that the owner raises the plurality of animals, wherein the plurality of animals that the owner raises include a plurality of different breeds, species or a combination thereof.

7. A non-transitory recording medium storing a display control program causing a computer to execute processing comprising:
receiving information which is notified from an information processing apparatus and indicates that an animal is infected with an infection disease; and
performing control for displaying images of a plurality of animals that an owner raises so as to discriminate which animal of the plurality of animals that the owner raises is infected with the infection disease based on the received information, in a case where it is determined that the owner raises the plurality of animals, wherein the plurality of animals that the owner raises include a plurality of different breeds, species or a combination thereof.

8. The display control device of claim 3, further comprising:
a determination unit that determines whether or not the infection disease is likely to infect an animal other than the animal to be inspected among the plurality of animals raised by the owner; and
a notification unit that notifies the owner of information indicating whether or not the infection disease is likely to infect the animal other than the animal to be inspected among the plurality of animals raised by the owner.

9. The display control method of claim 6, further comprising:
determining whether or not the infection disease is likely to infect an animal other than the animal to be inspected among the plurality of animals raised by the owner; and
notifying the owner of information indicating whether or not the infection disease is likely to infect the animal other than the animal to be inspected among the plurality of animals raised by the owner.

10. The non-transitory recording medium of claim 7, wherein the processing further comprises:
determining whether or not the infection disease is likely to infect an animal other than the animal to be inspected among the plurality of animals raised by the owner; and
notifying the owner of information indicating whether or not the infection disease is likely to infect the animal other than the animal to be inspected among the plurality of animals raised by the owner.

* * * * *